(12) United States Patent
Metzger et al.

(10) Patent No.: US 9,273,115 B2
(45) Date of Patent: Mar. 1, 2016

(54) METHOD FOR CONTROLLING THE BIOLOGICAL ACTIVITY OF A PROTEIN IN A VERTEBRATE CELL

(75) Inventors: Daniel Metzger, Strasbourg (FR);
Pierre Chambon, Blaesheim (FR);
Huimin Zhao, Champaign, IL (US);
John Katzenellenbogen, Urbana, IL (US)

(73) Assignees: CENTRE NATIONAL DE LA RECHERCHE SCIENTIFIQUE (CNRS), Paris (FR); THE BOARD OF TRUSTEES OF THE UNIVERSITY OF ILLINOIS, Urbana, IL (US); UNIVERSITE DE STRASBOURG, Strasbourg (FR)

( * ) Notice: Subject to any disclaimer, the term of this patent is extended or adjusted under 35 U.S.C. 154(b) by 350 days.

(21) Appl. No.: 13/145,752

(22) PCT Filed: Jan. 22, 2010

(86) PCT No.: PCT/EP2010/050723
§ 371 (c)(1),
(2), (4) Date: Sep. 22, 2011

(87) PCT Pub. No.: WO2010/084171
PCT Pub. Date: Jul. 29, 2010

(65) Prior Publication Data
US 2012/0052570 A1    Mar. 1, 2012

Related U.S. Application Data

(60) Provisional application No. 61/146,449, filed on Jan. 22, 2009.

(51) Int. Cl.
*C12N 15/00* (2006.01)
*C07K 14/72* (2006.01)
*C12N 9/90* (2006.01)

(52) U.S. Cl.
CPC ............... *C07K 14/721* (2013.01); *C12N 9/90* (2013.01); *C07K 2319/715* (2013.01)

(58) Field of Classification Search
None
See application file for complete search history.

(56) References Cited

U.S. PATENT DOCUMENTS

2006/0199250 A1   9/2006   Zhao et al.

FOREIGN PATENT DOCUMENTS

| EP | 1692936 A1 | 8/2006 |
|---|---|---|
| WO | 02/097050 A2 | 12/2002 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Ali et al., "Production and Characterization of Monoclonal Antibodies Recognising Defined Regions of the Human Oestrogen Receptor," Hybridoma, vol. 12, No. 4, 1993, pp. 391-405.

Anstead et al., "The estradiol pharmacophore: Ligand structure-estrogen receptor binding affinity relationships and a model for the receptor binding site," Steroids, vol. 62, 1997, pp. 268-303.
Brocard et al., "Spatio-temporally controlled site-specific somatic mutagenesis in the mouse," Proc. Natl. Acad. Sci., vol. 94, Dec. 1997, pp. 14559-14563.
Bush et al., "Use of the yeast one-hybrid system to screen for mutations in the ligand-binding domain of the estrogen receptor," Steroids, vol. 61, 1996, pp. 102-109.
Chockalingam et al., "Directed evolution of specific receptor-ligand pairs for use in the creation of gene switches," PNAS, vol. 102, No. 16, Apr. 19, 2005, pp. 5691-5696, XP-002508545.
Clifford et al., "RXRα-null F9 embryonal carcinoma cells are resistant to the differentiation, anti-proliferative and apoptotic effects of retinoids," The EMBO Journal, vol. 15, No. 16, 1996, pp. 4142-4155.
Ekena et al., "Determinants of Ligand Specificity of Estrogen Receptor-α: Estrogen versus Androgen Discrimination," The Journal of Biological Chemistry, vol. 273, No. 2, Jan. 9, 1998, pp. 693-699, XP-002575647.
Ekena et al., "Different Residues of the Human Estrogen Receptor are Involved in the Recognition of Structurally Diverse Estrogens and Antiestrogens," The Journal of Biological Chemistry, vol. 272, No. 8, Feb. 21, 1997, pp. 5069-5075, XP-002575646.
Ekena et al., "Identification of Amino Acids in the Hormone Binding Domain of the Human Estrogen Receptor Important in Estrogen Binding," The Journal of Biological Chemistry, vol. 271, No. 33, Aug. 16, 1996, pp. 20053-20059, XP-002075903.
Feil et al., "Regulation of Cre Recombinase Activity by Mutated Estrogen Receptor Ligand-Binding Domains," Biochemical and Biophysical Research Communications, vol. 237, No. 3, Jul. 7, 1997, pp. 752-757, Article No. RC977124, XP-002144708.
Feil, "Conditional Somatic Mutagenesis in the Mouse Using Site-Specific Recombinases," HEP, vol. 178, pp. 3-28 (2007).
Fink et al., "Novel structural templates for estrogen-receptor ligands and prospects for combinatorial synthesis of estrogens," Chemistry & Biology—Research Paper, http://biomednet.com/cbiology/cmb, pp. 205-219, (1999).
Fussenegger, "The Impact of Mammalian Gene Regulation Concepts on Functional Genomic Research, Metabolic Engineering, and Advanced Gene Therapies—Review," Biotechnol. Prog., vol. 17, No. 1, 2001, pp. 1-51.
Harvey et al., "Inducible control of gene expression: prospects for gene therapy," Current Opinion in Chemical Biology, vol. 2, 1998, pp. 512-518, http://biomednet.com/elecref/1367593100200512.
International Search Report (PCT Form PCT/ISA/210) for PCT/EP2010/050723 mailed Apr. 12, 2010.

(Continued)

*Primary Examiner* — Richard Hutson
(74) *Attorney, Agent, or Firm* — Birch, Stewart, Kolasch & Birch, LLP

(57) ABSTRACT

The present invention relates to a method for tightly temporally controlling the biological activity of a protein of interest in a vertebrate, upon induction of the activity of a fusion protein comprising said protein of interest and an ERM polypeptide containing a mutated ligand binding domain of the human oestrogen receptor α, with a synthetic ligand that does not interfere with oestrogen signalling. In particular, the present invention concerns a method for generating tightly temporally-controlled targeted somatic mutations in a vertebrate, preferably a mouse, by inducing the activity of a fusion protein comprising a site-specific recombinase protein and an ERM polypeptide, with a synthetic ligand devoid of oestrogenic and anti-oestrogenic activities.

14 Claims, 8 Drawing Sheets

(56) References Cited

OTHER PUBLICATIONS

Figure 1:
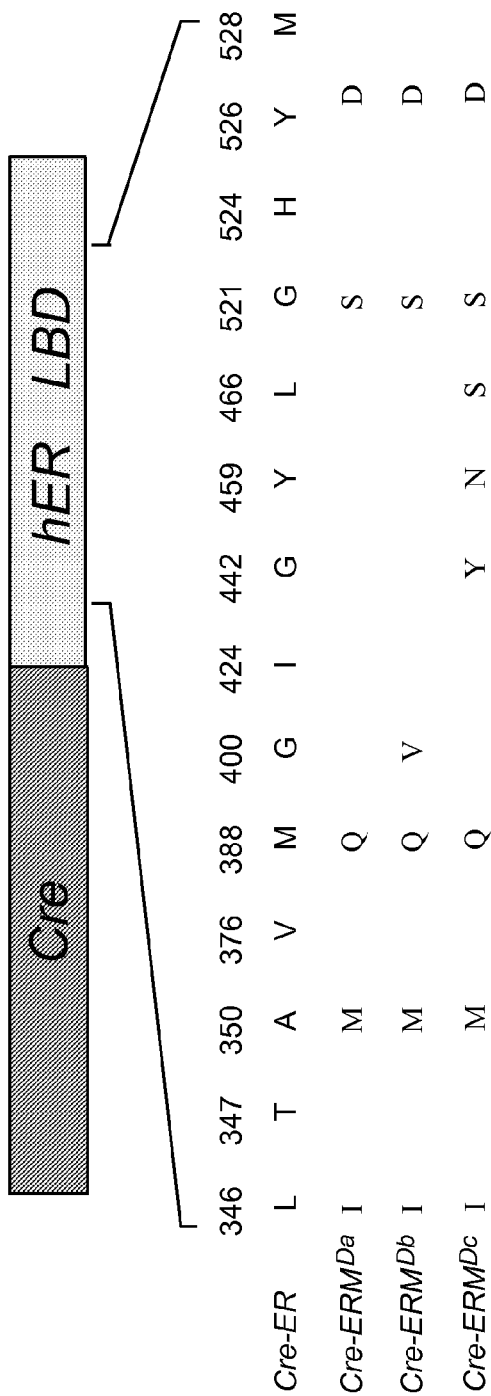

Islam et al., "Directed evolution of estrogen receptor proteins with altered ligand-binding specificities," Protein Engineering, Design & Selection, vol. 22, No. 1, 2009, pp. 45-52, XP-002575645.

Kellendonk et al., "Inducible Site-specific Recombination in the Brain," J. Mol. Biol., vol. 285, 1999, pp. 175-182.

Li et al., "Skin abnormalities generated by temporally controlled RXRα mutations in mouse epidermis," Letters to Nature, vol. 407, Oct. 5, 2000, pp. 633-636.

Mattioni et al., "Regulation of Protein Activities by Fusion to Steroid Binding Domains," Methods in Cell Biology, vol. 43, Chapter 16, pp. 335-352.

Metzger et al., "Conditional site-specific recombination in mammalian cells using a ligand-dependent chimeric Cre recombinase," Proc. Natl. Acad. Sci., vol. 92, Jul. 1995, pp. 6991-6995.

Metzger et al., "Site-and Time-Specific Gene Targeting in the Mouse," Methods, vol. 24, 2001, pp. 71-80.

Metzger et al., "Targeted Somatic Mutagenesis in the Mouse Epidermis," Methods in Molecular Biology, "Epidermal Cells: Methods and Protocols," vol. 289, No. 33, p. 329-340.

Picard, "Regulation of protein function through expression of chimaeric proteins," Current Opinion in Biotechnology, vol. 5, 1994, pp. 511-515.

Soriano, "Generalized lacZ expression with the ROSA26 Cre reporter strain," Nature Genetics, vol. 21, Jan. 1999, pp. 70-71.

Vassar et at "Tissue-specific and differentiation-specific expression of a human K14 keratin gene in transgenic mice," Proc. Natl. Acad. Sci., vol. 86, Mar. 1989, pp. 1563-1567.

Written Opinion (PCT Form PCT/ISA/237) for PCT/EP2010/050723 mailed Apr. 12, 2010.

Zambrowicz et al., "Knockouts Model the 100 Best-Selling drugs—will they model the next 100?" Nature Reviews/Drug Discovery, vol. 2, Jan. 2003, pp. 38-51.

\* cited by examiner

METHOD FOR CONTROLLING THE BIOLOGICAL ACTIVITY OF A PROTEIN IN A VERTEBRATE CELL

CROSS REFERENCE TO RELATED APPLICATIONS

This application is the National Phase of PCT/EP2010/050723 filed on Jan. 22, 2010, which claims the benefit under 35 U.S.C. 119(e) of U.S. Provisional Application No. 61/146,449 filed on Jan.22, 2009, all of which are hereby expressly incorporated by reference into the present application.

The present invention relates to a method for achieving a tight temporal control of the biological activity of a protein of interest in a vertebrate, by inducing the activity of a fusion protein between said protein of interest and a polypeptide (hereinafter "ERM polypeptide") comprising a mutated ligand binding domain (LBD) of the human oestrogen receptor α, through the binding of a synthetic ligand that does not interfere with oestrogen signalling.

In particular, the present invention concerns a method for obtaining tightly temporally-controlled targeted somatic mutations in a vertebrate, preferably a mouse, by inducing the activity of a fusion protein comprising a site-specific recombinase protein and an ERM polypeptide, with a synthetic ligand devoid of oestrogenic and anti-oestrogenic activities.

Sequencing of the human genome offers an unprecedented opportunity for the development of novel therapeutics. There might be as many as 10 000 new drug targets within the genome.

One major challenge of the biopharmaceutical industry is to delineate targets with the greatest value for therapeutic intervention. In this respect, genetically engineered mice (GEMs) generated by gene knock-out (KO) technology have proven to be very valuable for target discovery and validation (Zambrowicz and Sands, 2003). A retrospective study of KOs of genes encoding top drug targets has often shown a correlation between phenotypes, mechanism of action and utility of associated therapeutics (Zambrowicz and Sands, 2003). However, targeting a mutation in the germ line has some inherent limitations, such as problems associated with embryonic lethality, the occurrence of developmental aberrations, or compensatory effects by functionally redundant genes (Metzger and Chambon, 2001). Methods allowing the production of conditional gene targeting based on the properties of site-specific recombinases have been developed during the recent years. Spatio (i.e., cell/tissue specific)-temporally controlled targeted somatic mutagenesis has been achieved in the mouse by combining the Cre/LoxP system with the tetracyclin system. However, in a number of cases, Cre expression is not sufficiently tightly regulated, and generating such mice requires complex and time-consuming breedings (Feil, 2007). The development of chimeric site-specific recombinases, the activity of which is ligand-inducible has facilitated the production of spatio-temporally-controlled somatic mouse mutants (see U.S. Pat. No. 7,112,715 B2 issued on Sep. 26, 2006). The most efficient and widely used system relies on induction by Tamoxifen (Tam), a synthetic ligand endowed with anti-oestrogenic activity, of the recombinase activity of Cre-ER$^{T2}$, a fusion protein between the Cre recombinase and a triple-mutated LBD of the human oestrogen receptor α (see EP Patent No. 1 692 936 B1 published on Jun. 25, 2008). Indeed, in contrast to other Cre-LBD fusion proteins, Cre-ER$^{T2}$ exhibits no background recombinase activity in the absence of the ligand, and its recombinase activity is induced by low doses of Tam and short periods of treatment. However, this system suffers from the complex agonistic/antagonistic activities of Tam on endogenous oestrogen receptors, which appear to undesirably interfere with phenotypic analyses of the generated somatic mutant mice. Such undesirable side effects may be referred as "ligand toxicity" or "ligand side effect".

Such side effects may also prevent the use of ligand-inducible chimeric proteins as therapeutic agents in gene therapy (Picard, 1994; Fussenegger, 2001).

There is therefore a need for developing a system in which a fused LBD would tightly block the activity of a protein of interest, while the cognate LBD ligand, the addition of which restores the activity of the protein, is devoid of any physiological or patho-physiological deleterious effects. Such a system should be particularly useful for targeted spatio-temporally controlled somatic mutagenesis.

These needs are satisfied for the first time by the methods according to the present invention which overcome the major disadvantages and limits of currently available methods.

Mutant LBDs of the human oestrogen receptor α that selectively bind cognate synthetic ligands devoid of oestrogenic activity have been reported (Chockalingam et al., 2005; U.S. Patent Application No. 2006/0199250 published on Sep. 7, 2006). In particular, Chockalingam et al. described in 2005 two LBDs of the human oestrogen receptor α having the following mutations: L346I, A350M, M388Q, G521S, Y526D ("mutant 4-S"), and L346I, A350M, M388Q, G521S, Y526D, F461L, V560M ("mutant 5-E"). These mutants were shown to be highly selective for the synthetic non-steroidal compound 4,4'-dihydroxybenzil (DHB) compared to the natural ligand 17β-estradiol ($E_2$). However, they did not respond to DHB with a potency fully equivalent to that of the wild-type human oestrogen receptor α-$E_2$ response. In addition, as illustrated in the Examples hereinafter, mutant 4-S fused to the Cre recombinase (corresponding to the Cre-ERM$^{Da}$ construct) does not prevent background recombinase activity in the absence of DHB.

The Inventors have discovered that it was possible to significantly improve the methods available to date for controlling protein activity in vertebrate cells, by using LBDs of the human oestrogen receptor α that: (i) harbour original mutations or sets of mutations; (ii) are specifically bound by synthetic ligands devoid of any effect on oestrogen-involving metabolic pathways; (iii) show significantly improved potency and/or selectivity for the corresponding synthetic ligands; and (iv) allow protein activity to be obtained in the targeted cells upon induction by the corresponding synthetic ligands only (leading to a tight temporal control). In a working example described in detail below, the Inventors tested and were able to select original pairs of specific ERMs and synthetic ligands, to be used, e.g., for potently and advantageously replacing the previously described pair of the ER$^{T2}$ triple-mutated LBD and Tamoxifen, as an improved recombination system.

A first aspect of the present invention relates to a method for tightly temporally controlling the biological activity of a protein of interest in at least one targeted cell of a vertebrate, said protein of interest being expressed in said targeted cell in the form of a fusion protein comprising:

(i) an ERM polypeptide selectively binding a synthetic ligand devoid of oestrogenic and anti-oestrogenic activities, and comprising a mutated form of the ligand binding domain of the human oestrogen receptor α, said mutated form having at least six amino-acid substitutions at positions, relative to the wild-type form of said ligand binding domain: L346, A350, M388, G521, Y526, and at least one additional position selected from: T347, V376, G400, I424, G442, Y459, L466, H524, and M528, and (ii) said protein of interest, the biological activity of which is induced by said synthetic ligand, wherein said method comprises:

a) providing a vertebrate targeted cell expressing said fusion protein;

b) contacting said vertebrate targeted cell with said synthetic ligand in order to induce the biological activity of said fusion protein in said cell; and c) recovering the biological activity of said fusion protein in said vertebrate targeted cell.

The method according to the present invention enables one to tightly temporally control the biological activity of a protein of interest. In this respect, a "tight temporal control" means that the biological activity is obtained upon induction by an appropriate synthetic ligand only; there is no significant background level of biological activity in the absence of ligand (e.g., less than 5% compared to the efficiency observed in the presence of said synthetic ligand).

As indicated above, an "ERM polypeptide" is a mutated oestrogen receptor that is capable of selectively binding a synthetic ligand devoid of oestrogenic and anti-oestrogenic activities, and that comprises a mutated form of the ligand binding domain of the human oestrogen receptor α.

The term "mutation" is understood to mean any changes occurring in the sequence of the human nuclear oestrogen receptor α, other than those present in its natural variants and/or in its human or vertebrate homologues, and which substantially modify the biological activity of the protein of interest fused to the ERM polypeptide, in response to the binding of an appropriate synthetic ligand.

Such mutations may be point mutations, deletions, insertions, substitutions. Of course, for the purposes of the present invention, only are selected mutations in the LBD of the human oestrogen receptor α that will permit to: (i) induce the biological activity of the protein of interest fused to the ERM polypeptide upon exposure to the cognate synthetic ligand; (ii) avoid background biological activity in the absence of said synthetic ligand.

In the context of the present invention, the mutated form of the ligand binding domain of the human oestrogen receptor α has at least one amino-acid substitution at a position selected from, relative to the wild-type form of said ligand binding domain: L346, T347, A350, V376, M388, G400, I424, G442, Y459, L466, G521, H524, Y526, and M528. In particular, said mutated form has at least six amino-acid substitutions at positions, relative to the wild-type form of said ligand binding domain: L346, A350, M388, G521, Y526, and at least one additional position selected from: T347, V376, G400, I424, G442, Y459, L466, H524, and M528. Yet in particular, said additional position is selected from: G400, G442, Y459, and L466.

For instance, said mutated form is substituted at the following positions:

L346, A350, M388, G521, and Y526;

L346, A350, M388, G400, G521, and Y526; and

L346, A350, M388, G442, Y459, L466, G521, and Y526.

Preferred mutations are selected from: L346I, T347C, A350M, V376A, M388Q, M388F, I424V, G442Y, Y459N, L466S, G521S, G521R, H524Y, Y526D, and M528E.

Appropriate ERM polypeptides are preferably chosen from:

ERM$^{Da}$ yet described as mutant 4-S in Chockalingam et al. (2005), said mutant harbouring the following mutations: L346I, A350M, M388Q, G521S, and Y526D;

ERM$^{Db}$ having the following mutations: L346I, A350M, M388Q, G400V, G521S, and Y526D; and ERM$^{Dc}$ having the following mutations: L346I, A350M, M388Q, G442Y, Y459N, L466S, G521S, and Y526D.

Yet preferred ERM polypeptides are chosen from ERM$^{Db}$ and ERM$^{Dc}$.

Are not within the scope of the present invention the ERM mutants described in Chockalingam et al. (2005) and in U.S. Patent Application No. 2006/0199250 published on Sep. 7, 2006, when fused to the DNA binding domain of the yeast Gal4 transactivator. In particular, the following fusion proteins are excluded from the scope of the present invention: anyone of the ERM polypeptides 1-S, 2-S, 3-S, 4-S, 5-E, 5-S, 6-S, and 7-E (as named in US 2006/0199250) fused to the yeast Gal4 transactivator.

The expression "synthetic ligand" is understood to encompass any type of compound capable of binding to the ERM polypeptide, preferably with high affinity, said compound being devoid of oestrogenic and anti-oestrogenic activities. This means that the synthetic ligand does not interfere with oestrogen signaling pathway in the cell, tissue, organ or vertebrate organism. In particular, the synthetic ligand does not have agonistic/antagonistic activities on the endogenous oestrogen receptor. Thus, using such a synthetic ligand prevents any undesirable pleiotropic interference of the receptor-ligand combination with regulatory networks in the host cell, tissue, organ, or organism. This is an essential feature of the synthetic ligands according to the present invention not to cross-interact with host regulatory pathways. In the context of the present invention, it will be preferred to use a low dose (or a small quantity) of said synthetic ligand in order to induce the protein activity of interest. Suitable synthetic ligands are, for example, the synthetic nonsteroidal compound 4,4'-dihydroxybenzyl (DHB), 4,4'-dihydroxybenzyl dipivalate (DH BD), 4-hydroxy-4'-methoxybenzyl (HMB), 4,4'-methoxybenzyl (MB), and 2,4-di(4-hydroxyphenyl)-5-ethylthiazole (L9; Fink et al., 1999).

In the method of the invention, the vertebrate targeted cell is contacted with the synthetic ligand in order to induce, in said cell, the biological activity of the fusion protein.

The terms "a small quantity of synthetic ligand" mean that the efficient dose of synthetic ligand to administer is low. The expressions "small quantity", "small amount", and "low dose" are equivalent. The term "low" or "small" is understood to mean quantities of less than or equal to 5 mg/adult mouse/day, preferably less than or equal to 4 mg/adult mouse/day, yet preferably less than or equal to 2 or 1 mg/adult mouse/day. According to an even more preferred embodiment, this quantity may be less than or equal to 0.5 mg, 0.25 mg, 0.10 mg, 0.075 mg, 0.05 mg, 0.025 mg, 0.001 mg per adult mouse and per day. Of course, it is understood that the person skilled in the art is able to adjust these quantities, according to the vertebrate under consideration, its weight and its age.

It is possible to administer a synthetic ligand, by the method of the invention, either to a vertebrate organism, or to an organ or to a tissue or to a cell thereof. In practice, one can bring a vertebrate targeted cell into contact with said synthetic ligand by oral or topical administration, or by injection such as intravenous, intramuscular, intraspinal, intracerebral, intraperitoneal injection. In the case of an embryo, a fetus or a neonate before weaning, the treatment with the synthetic ligand may be carried out by administration to the mother.

When this involves cells in culture derived from a vertebrate organism, the synthetic ligand is preferably added to the culture medium, or injected into the targeted cell. By doing so, it is thus possible to, e.g., inactivate or modify a gene or an intergenic sequence of interest when desired (temporal control) in a given cell or tissue or organ (spatial control), for, inter alia, studying the function of this gene or of this intergenic sequence at various periods during development or post-natally.

To an ERM polypeptide corresponds at least one synthetic ligand. Reciprocally, to a synthetic ligand corresponds at least one ERM polypeptide. Preferably, to an ERM polypeptide corresponds one synthetic ligand. This means that the ERM polypeptide and the synthetic ligand are cognate partners that specifically and selectively bind to and interact with each other so as to form a functional pair.

"Proteins of interest" suitable for use in the context of the present invention include, but are not limited to, industrial and pharmaceutical proteins, cell surface receptors, antigens, antibodies, cytokines, hormones, transcription factors, signaling modules, cytoskeletal proteins, enzymes, oncogenes and tumor-suppressor genes (Mattioni et al., 1994; Harvey and Caskey, 1998; Picard, 1994). Non-limiting examples of such proteins of interest are given in U.S. patent application No. U.S. 2006/0199250.

Preferably, the "protein of interest" is a recombinase protein. Yet preferably, said recombinase protein is a site-specific recombinase protein selected from the group consisting of: the Cre recombinase of bacteriophage P1, the FLP recombinase of *Saccharomyces cerevisiae*, the R recombinase of *Zygosaccharomyces rouxii* pSR1, the A recombinase of *Kluyveromyces drosophilarium* pKD1, the A recombinase of *Kluyveromyces waltii* pKW1, the integrase λInt, the recombinase of the GIN Recombination system of the Mu phage, the bacterial β recombinase, and variants thereof. Yet more preferably, the protein of interest is the Cre recombinase protein. Thus, suitable fusion proteins comprise, in the context of the present invention, the Cre recombinase protein fused to anyone of the ERM polypeptides disclosed herein. Yet preferred fusion proteins are chosen from: Cre-ERM$^{Da}$, Cre-ERM$^{Db}$, and Cre-ERM$^{Dc}$. According to the present invention, a "vertebrate" is selected from: birds, fishes, and mammals including humans, bovines, porcines, caprines, ovines, equines, rodents such as mice and rats. Preferably, a vertebrate is a mouse.

A "targeted cell" is a cell expressing a fusion protein between an ERM polypeptide and a protein of interest. In such a targeted cell, the protein of interest comprised in the fusion protein is expressed but it remains inactive until exposure to an appropriate synthetic ligand. To target a cell, use is made of expression elements ensuring a spatially controlled expression in the targeted cell. In particular, use is made of a promoter for directing the expression of the fusion protein in the targeted cell or tissue or organ.

The fusion protein is preferably encoded by a fusion gene under the control of expression elements ensuring a spatially controlled expression thereof in said targeted cell. The terms "expression elements ensuring a spatially controlled expression" are understood to mean at least one of the DNA sequences involved in gene expression regulation, including promoter or minimal promoter sequences, upstream sequences, activating sequences ("enhancers"), inhibitory sequences ("silencers"), "insulator" sequences, and the like.

Appropriate "promoter sequences" (or "promoter regions" or "promoters") may be chosen from those promoter sequences that make it possible to obtain a specific, and preferably high, protein expression in one or more cells, tissues, cell types or organs. These promoters may be heterologous to the vertebrate under consideration, or they may be naturally present in the genome of the vertebrate.

Thus, preferably, the fusion gene is placed under the control of tissue-specific or cell-specific or ubiquitous expression elements.

For more details, the person skilled in the art can refer to the teaching in U.S. Pat. No. 7,112,715.

In an embodiment, the fusion protein is encoded by a fusion gene integrated into one or more of the chromosomes of said cell of said vertebrate. In another embodiment, the fusion protein is encoded by a fusion gene integrated into an expression vector. The fusion gene may be introduced into the cell in the form of an expression vector or of one of its fragments. A "vector" is a replicon wherein another polynucleotide segment (i.e., the fusion gene) is attached, so as to bring the replication and/or expression to the attached segment. The vector may be, for instance, a bacterial plasmid DNA, a cosmid, a phage DNA, a viral DNA or a minichromosome (BAC, YAC, and the like). Such a vector may be integrative, which means that it is able to integrate into the genome of the host cell or it may exist in the form of an extrachromosomal replicon. In the latter case, the expression vector is capable of replicating autonomously. When using a fragment of an expression vector, this fragment preferably integrates into the cell genome. The expression vector, or one of its fragments, comprises at least the fusion gene and a promoter and/or expression elements making it possible to direct and control the expression of the fusion protein in the targeted cell.

Advantageously, the expression vector further comprises signals for transcription initiation and termination, as well as appropriate regions for transcription regulation. These various control signals are chosen according to the vertebrate cell type that is used.

Construction of any vector in the context of the invention uses recombinant DNA technologies that are well known by a person skilled in the art. Standard techniques are used for cloning, isolation of DNA, amplification and purification; enzymatic reactions involving DNA ligase, DNA polymerase, restriction endonucleases are carried out according to the manufacturer's recommendations.

When a vector is used, it may be introduced into the targeted cell by standard methods such as microinjection into a pronucleus, transfection by calcium phosphate precipitation, lipofection, electroporation, heat shock.

Alternatively, the fusion protein may be directly introduced into the vertebrate organism, or into a targeted cell of said vertebrate organism, typically by injection into a tissue or an organ in the case of an organism, or by microinjection in the case of a cell.

Thus, the method according to the present invention enables one to obtain a transgenic vertebrate, in particular a transgenic mouse: (i) which expresses a fusion protein in a tissue-specific manner in one or more cell types thereof; (ii) wherein the biological activity of a protein of interest comprised in said fusion protein is negligible, or even zero, in the absence of a specific synthetic ligand devoid of oestrogenic and antioestrogenic activities; (iii) wherein said biological activity is activated (induced) by a low dose of said synthetic ligand (e.g., from 0.001 to 5 mg of ligand/mouse/day, during for instance 5 days); and (iv) wherein said biological activity is satisfyingly efficient.

A "satisfyingly efficient biological activity" means that this activity is of at least 85%, 90%, 92%, 94%, 95%, 96%, 97%, 98%, 99%, 100% compared to the native protein (i.e., the protein when not fused to an ERM polypeptide), in the targeted cells expressing the fusion protein, in the presence of a synthetic ligand devoid of oestrogenic and anti-oestrogenic activities, whereas, in these cells, the efficiency is at least less than 5%, 4%, 3%, 2%, 1%, 0.5%, 0.1%, 0.01%, or zero in the absence of said synthetic ligand relative to the efficiency observed in the presence of said synthetic ligand under the same conditions.

As an example, when the protein of interest is a recombinase, the method enables one to control DNA recombinations in targeted cells. The present invention makes it thus possible to carry out spatio-temporally controlled site-specific DNA recombinations, with an efficiency of at least 85%, 90%, 92%, 94%, 95%, 96%, 97%, 98%, 99%, to 100%, in the targeted cells expressing the fusion protein, in the presence of a synthetic ligand devoid of oestrogenic and anti-oestrogenic activities, whereas, in these cells, the efficiency is at least less than 5%, 4%, 3%, 2%, 1%, 0.5%, to 0.1%, 0.01%, or zero in the absence of said synthetic ligand. This means that, when the protein of interest is a recombinase, the present invention makes it possible to carry out spatio-temporally controlled site-specific DNA recombinations in at least 85%, 90%, 92%, 94%, 95%, 96%, 97%, 98%, 99%, 100% of the targeted cells expressing the fusion protein in the presence of a synthetic ligand devoid of oestrogenic and antioestrogenic activities, whereas at least less than 5%, 4%, 3%, 2%, 1%, 0.5%, 0.1%, 0.01%, or zero targeted cells undergo recombination in the absence of said synthetic ligand.

The DNA recombination efficiency may be estimated by techniques known to the person skilled in the art. Typically, this efficiency is estimated by the frequency of recombination events catalyzed by the recombinase. These events may be revealed by PCR or Southern Blotting and the recombination frequency may be estimated by determining the ratio of representation of the various alleles in the cells of a tissue. The frequencies of the various alleles may be estimated via an electrophoresis gel, by determining the intensity of the bands corresponding to a product of PCR amplification, or via quantitative PCR, or of genomic DNA (Southern blotting). The use of PCR makes this method of estimation extremely sensitive and makes it possible to detect the presence of cells whose genome has not undergone DNA recombination. Alternatively, a way of estimating the recombination efficiency uses immunohistochemistry, wherein for example the expression level of the product of a gene to be inactivated is analyzed.

In embodiments wherein the biological activity of more than one protein of interest is to be tightly temporally controlled in at least one targeted cell of a vertebrate, each protein of interest is expressed in said vertebrate targeted cell in the form of a fusion protein comprising:

said protein of interest, and a distinct and specific ERM polypeptide, said ERM polypeptide being selectively bound by a cognate synthetic ligand that may be the same for all the fusion proteins, or that may be different for each of the fusion proteins.

As yet mentioned above, the protein of interest is preferably a recombinase protein. Recombinase proteins are known to catalyze recombination reactions between two specific recognition sites (typically, Cre/Lox and FLP/FRT are among the most widely used systems). Here, in practice, the vertebrate targeted cell further comprises one or more recognition sites for said recombinase protein.

In a particular embodiment, said recombinase protein is the FLP recombinase of Saccharomyces cerevisiae and said recognition sites are the FRT sequences. Alternatively, and preferably, said recombinase protein is the Cre recombinase of bacteriophage P1 and said recognition sites are selected from the group consisting of: the sequences Lox P, Lox 66, Lox 71, Lox 511, Lox 512, and Lox 514.

Insertion of the recognition sites specific for a recombinase protein, in particular the loxP site(s) for the Cre recombinase, for recombination of a DNA sequence may be carried out by homologous recombination of the native region comprising said DNA sequence to be recombined [i.e., either excised or inverted (involving at least two two recognition sites in cis), or inserted or translocated (involving at least one recognition site in cis)] with the same region having been modified in such a way that it contains in 5' and/or 3' said recognition site(s), in particular loxP site(s).

The DNA sequence of interest bearing the recognition sites may otherwise be integrated at random.

For more details, the person skilled in the art can refer to the teaching in U.S. Pat. No. 7,112,715.

A preferred embodiment of the method of the present invention is thus for carrying out spatio-temporally-controlled site-specific recombinations of said DNA sequences of interest in a vertebrate. In this respect, in step c) of the method described above, recombination of said DNA sequences of interest is obtained in said vertebrate targeted cell.

"Recombinations" or "DNA recombinations" are to be understood according to the usual definition in the field. Typically, "recombinations" are selected from: excisions, insertions, inversions, deletions, and translocations.

A second aspect of the present invention relates to a method for carrying out spatio-temporally-controlled site-specific recombinations in at least one targeted cell of a vertebrate, of at least one DNA sequence of interest, said recombinations being mediated by at least one recombinase expressed in said targeted cell in the form of a fusion protein comprising:

(i) an ERM polypeptide selectively binding a synthetic ligand devoid of oestrogenic and anti-oestrogenic activities, and comprising a mutated form of the ligand binding domain of the human oestrogen receptor α, said mutated form having at least one amino-acid substitution at a position selected from, relative to the wild-type form of said ligand binding domain: L346, T347, A350, V376, M388, G400, I424, G442, Y459, L466, G521, H524, Y526, and M528, and (ii) said recombinase, the activity of which is induced by said synthetic ligand, wherein said method comprises:

a) providing a vertebrate targeted cell expressing said fusion protein;

b) contacting said vertebrate targeted cell with said synthetic ligand in order to induce the recombinase activity of said fusion protein in said cell; and c) obtaining recombination of said DNA sequence of interest in said vertebrate targeted cell.

For instance, said recombination may be carried out in the epidermis, and more precisely in keratinocytes, in the adipocytes, in the melanocytes or in the hepatocytes.

According to a third aspect, the present invention concerns various means that may be used in, or obtained by, the methods described above.

One of these means is a fusion protein.

In a first embodiment, this fusion protein comprises:

(i) an ERM polypeptide selectively binding a synthetic ligand devoid of oestrogenic and anti-oestrogenic activities, and comprising a mutated form of the ligand binding domain of the human oestrogen receptor α, said mutated form having at least six amino-acid substitutions at positions, relative to the wild-type form of said ligand binding domain: L346, A350, M388, G521, Y526 and at least one additional position selected from: T347, V376, G400, I424, G442, Y459, L466, H524, and M528 (in particular, said additional position is selected from: G400, G442, Y459, and L466), and (ii) a protein of interest, the biological activity of which is induced by said synthetic ligand, wherein, upon expression in at least one cell or cell type of a vertebrate, said fusion protein has a negligible, or even zero, biological activity in the absence of said synthetic ligand devoid of oestrogenic and anti-oestrogenic activities, and wherein said biological activity is induced by said synthetic ligand.

In a second embodiment, the fusion protein of the invention comprises:

(i) an ERM polypeptide selectively binding a synthetic ligand devoid of oestrogenic and anti-oestrogenic activities, and comprising a mutated form of the ligand binding domain of the human oestrogen receptor α, said mutated form having at least one amino-acid substitution at a position selected from, relative to the wild-type form of said ligand binding domain: L346, T347, A350, V376, M388, G400, I424, G442, Y459, L466, G521, H524, Y526, and M528, and (ii) a recombinase protein, the activity of which is induced by said synthetic ligand, wherein, upon expression in at least one cell or cell type of a vertebrate, said fusion protein has a negligible, or even zero, recombinase activity in the absence of said synthetic ligand devoid of oestrogenic and anti-oestrogenic activities, and wherein said recombinase activity is induced by said synthetic ligand.

Such fusion proteins have been described in detail above. In particular, preferred ERM polypeptides are chosen from ERM$^{Db}$ and ERM$^{Dc}$, and preferred fusion proteins are chosen from: Cre-ERM$^{Da}$, Cre-ERM$^{Db}$ and Cre-ERM$^{Dc}$.

In practice, such a fusion protein is encoded by a fusion gene, that is also encompassed a subject-matter of the present invention, as are an expression vector comprising said fusion gene, and a vertebrate host cell comprising said fusion gene or said expression vector.

Is further included in the scope of the present invention, a vertebrate model, with the exception of humans, comprising at least one of a fusion protein, a fusion gene, an expression vector, or a host cell as described above. A preferred vertebrate model is a mouse model.

The present invention is also related to a kit for use in a method as defined above, said kit comprising at least one of a fusion protein, a fusion gene, an expression vector, a host cell, and a vertebrate model as described above.

In further aspects, the present invention concerns uses of the means provided herein, including the foregoing fusion proteins, fusion genes, expression vectors, host cells, vertebrate models, and kits.

More particularly, anyone of said means is used for:
analyzing or studying the biological function of a DNA sequence of interest;
screening for candidate compounds useful for treating and/or preventing pathological conditions or disorders associated with alteration of the expression and/or of the function of a DNA sequence of interest;
gene therapy.

Preferably, for the purposes of gene therapy, the vertebrate targeted cell will be a human cell.

Various interesting applications are disclosed in U.S. Pat. No. 7,112,715, and the person skilled in the art will refer thereto if need be.

The following figures are provided for illustrating some embodiments and advantages of the present invention, in relation with the examples below.

FIG. 1. Schematic representation of the Cre-ERM mutant proteins. The position of the hERα mutated amino acids in the various fusion proteins is indicated.

Figure 2:
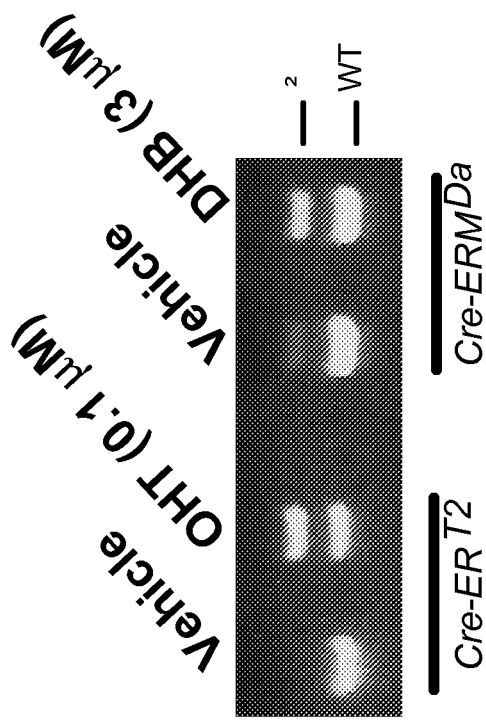

FIG. 2. PCR detection of Cre-ERM$^{Da}$-mediated floxed DNA excision in F9 cells. DNA from Cre-ER$^{T2}$/RXRα$^{+/(LNL)}$ cells treated with vehicle (ethanol) and 4-hydroxytamoxifen (OHT) and Cre-ERM$^{Da}$/RXRα$^{+/(LNL)}$ cells treated with vehicle (ethanol) and DHB (3 µM), was analysed by PCR. PCR products corresponding to the RXRα WT allele and Cre-mediated excised allele (Δ) are indicated.

Figure 3:
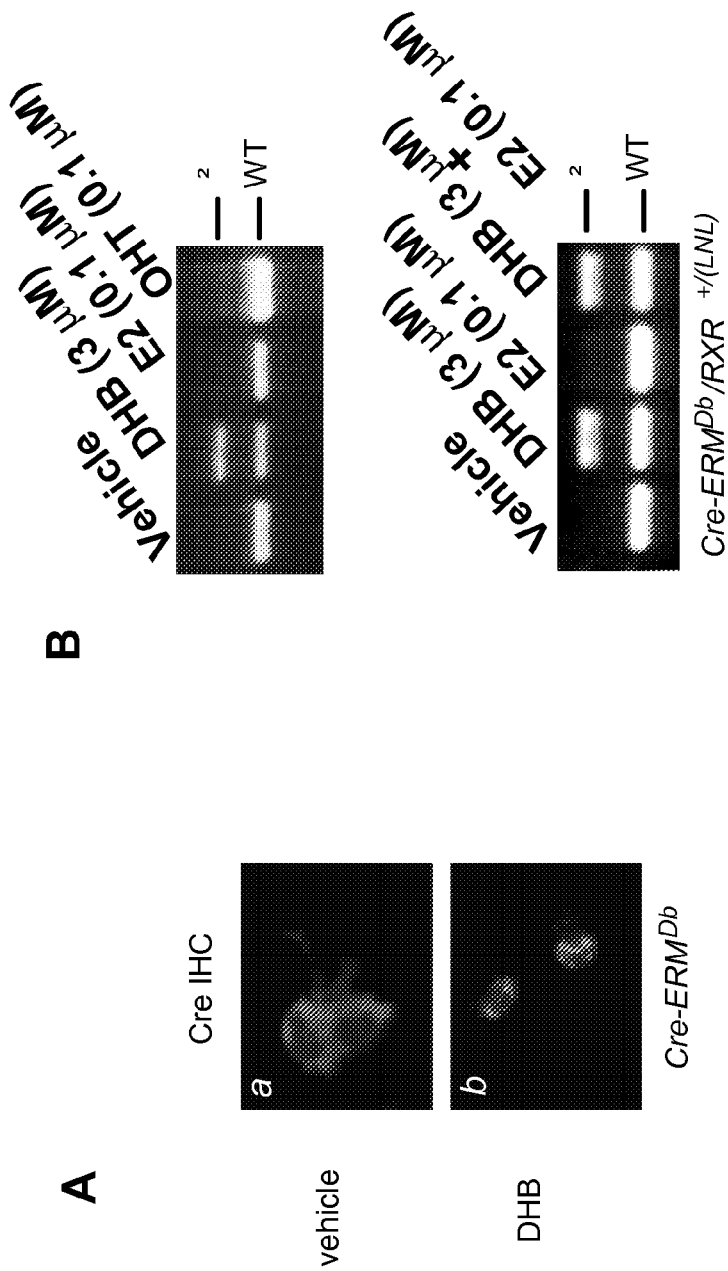

FIG. 3. (A) Immunocytochemistry with anti-Cre antibody was performed on pCre-ERM$^{Db}$-transfected Cos-1 cells, after vehicle (a) or DHB (b) treatment. The fluorescence corresponds to staining of Cre-ERM$^{Db}$. (B) PCR detection of Cre-ERM$^{Db}$-mediated floxed DNA excision in F9 cells. DNA from Cre-ERM$^{Db}$/RXRα$^{+/(LNL)}$ cells treated with vehicle (ethanol), DHB (3 µM), E2 (0.1 µM), OHT (0.1 µM) or DHB (3 µM) and E2 (0.1 µM) was analysed by PCR. PCR products corresponding to the RXRα WT allele and Cre-mediated excised allele (Δ) are indicated.

Figure 4:
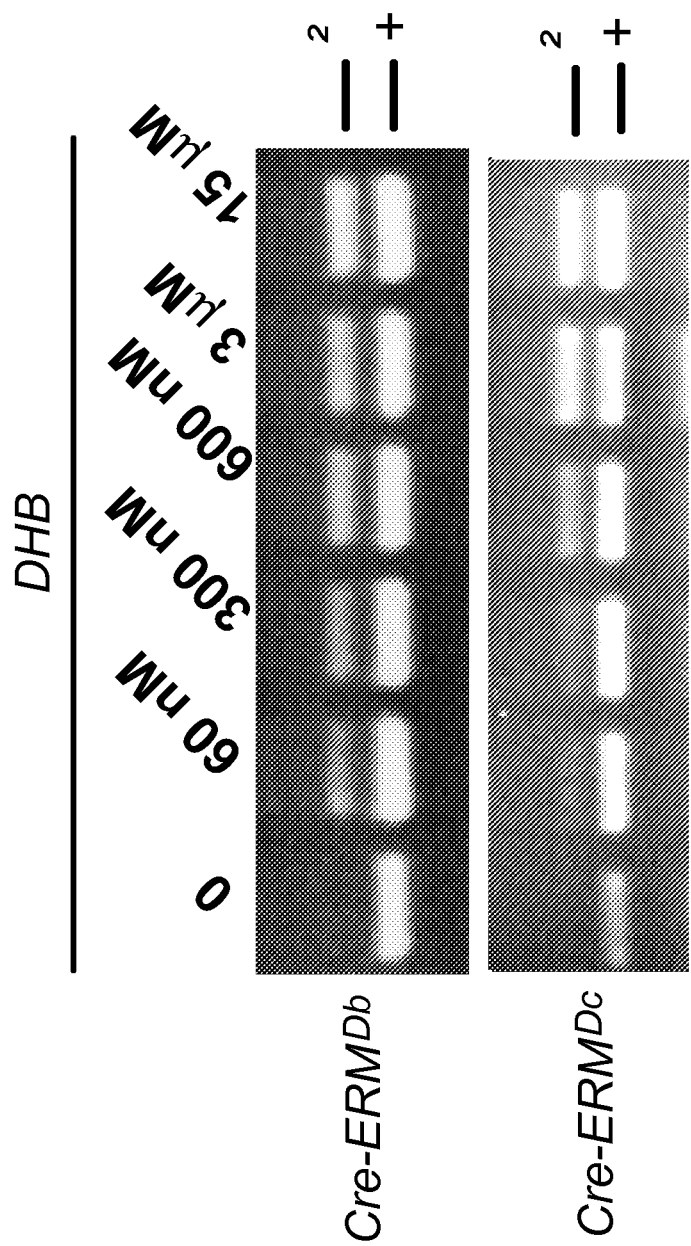

FIG. 4. Dose-response of the recombinase activity of Cre-ERM$^{Db}$ and Cre-ERM$^{Dc}$ in the presence of increasing amounts of DHB. DNA from Cre-ERM$^{Db}$/RXRα$^{+/(LNL)}$ and Cre-ERM$^{Dc}$/RXRα$^{+/(LNL)}$ cells treated with vehicle (ethanol; 0) and DHB (60 nM-15 µM) was analysed by PCR. PCR products corresponding to the RXRα WT allele and Cre-mediated excised allele (Δ) are indicated.

Figure 5:
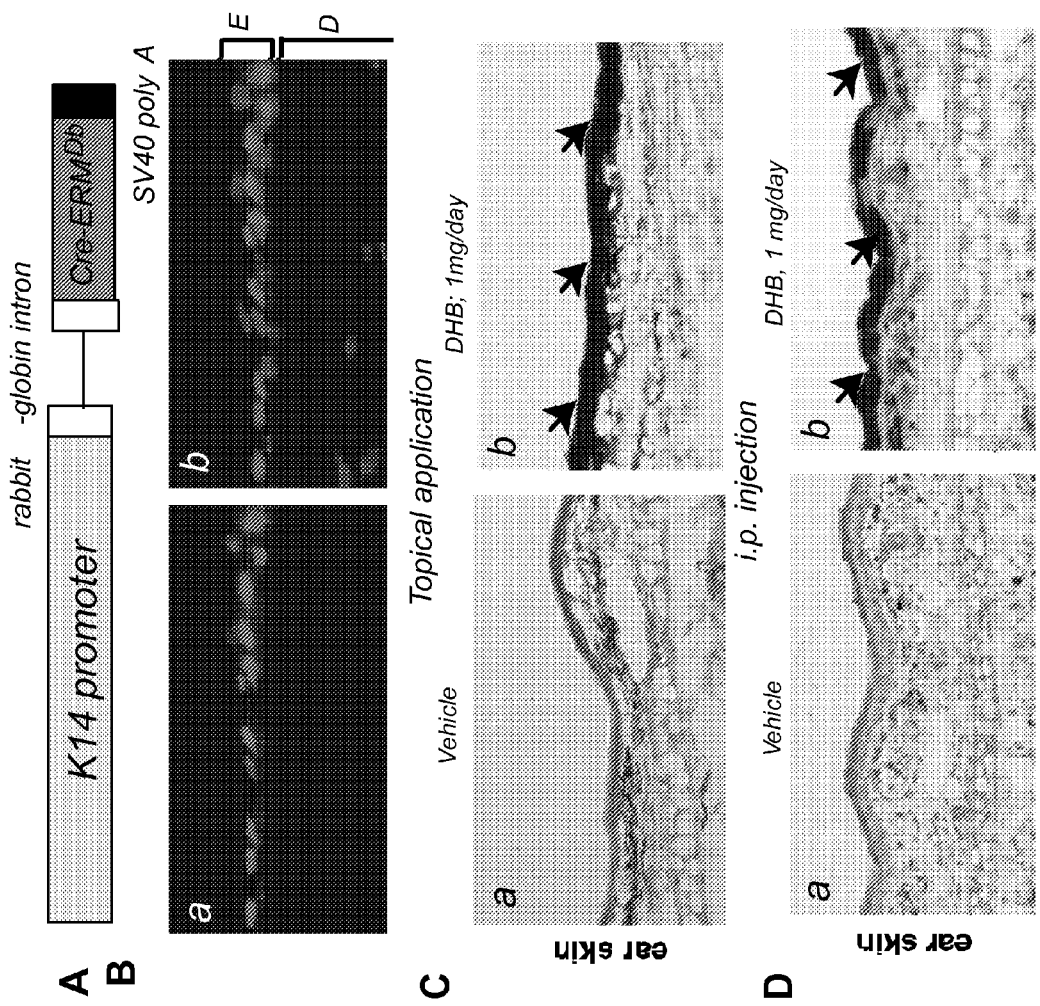

FIG. 5. Characterisation of Cre-ERM$^{Db}$ recombinase activity in epidermal keratinocytes of K14-Cre-ERM$^{Db}$ mice. (A) Schematic representation of the K14-Cre-ERM$^{Db}$ transgene. The K14 promoter region and the Cre-ERM$^{Db}$ coding region are represented by light and dark grey boxes, respectively. The rabbit β-globin intervening sequences (white boxes and black line) and SV40 polyadenylation sites (black box) are also indicated. (B) Immunohistochemical detection of Cre-ERM$^{Db}$ in epidermal keratinocytes. Immunohistochemistry with anti-Cre antibody was performed on ear sections from K14-Cre-ERM$^{Db}$ mice, 2 hrs after the fifth DHB topical application. The fluorescence in (a) corresponds to the staining of Cre-ERM$^{Db}$, and in (b) to the DAPI staining of the nuclei. E, epidermis; D, dermis. (C) DHB-induced Cre-ERM$^{Db}$ recombinase activity in ear keratinocytes of K14-Cre-ERM$^{Db}$/RosaR26R mice. X-Gal staining of ear section taken at day 12 from K14-Cre-ERM$^{Db}$/RosaR26R mice, daily topically ear-treated with vehicle (a) and DHB (1 mg/day) (b) from day 1 to day 5. (D) X-Gal staining of ear skin section taken at day 12 from K14-Cre-ERM$^{Db}$/RosaR26R, daily i.p. injected with vehicle (a) and DHB (1 mg/day) (b) from day 1 to day 5. Arrows point to some of the X-Gal stained keratinocytes in C(b) and D(b).

Figure 6:
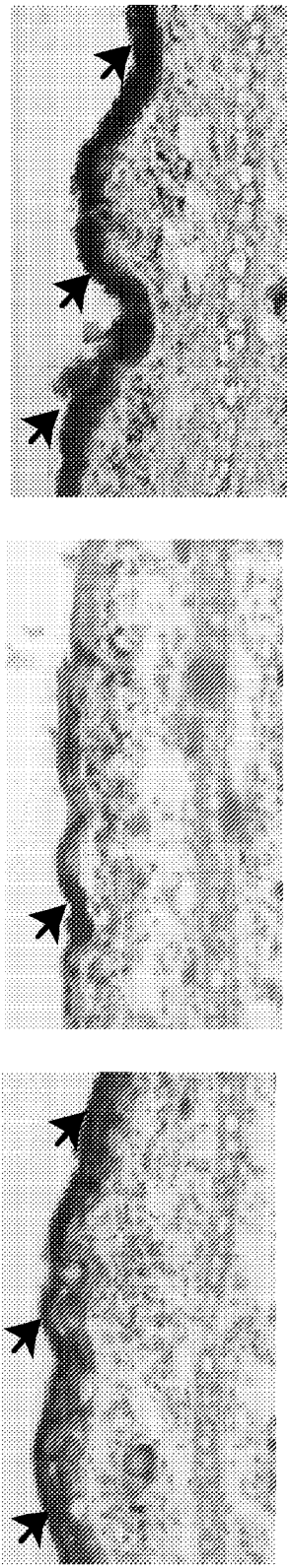

FIG. 6. Induction of Cre-ERM$^{Db}$ recombinase activity in skin keratinocytes of K14-Cre-ERM$^{Db}$/RosaR26R mice by various non-oestrogenic ligands. X-Gal staining of ear sections taken at day 12 from K14-Cre-ERM$^{Db}$/RosaR26R mice, daily topically ear-treated with 1 mg/day from day 1 to day 5 with DHB, HMB and MB. Arrows point to some of the X-Gal stained keratinocytes.

Figure 7:
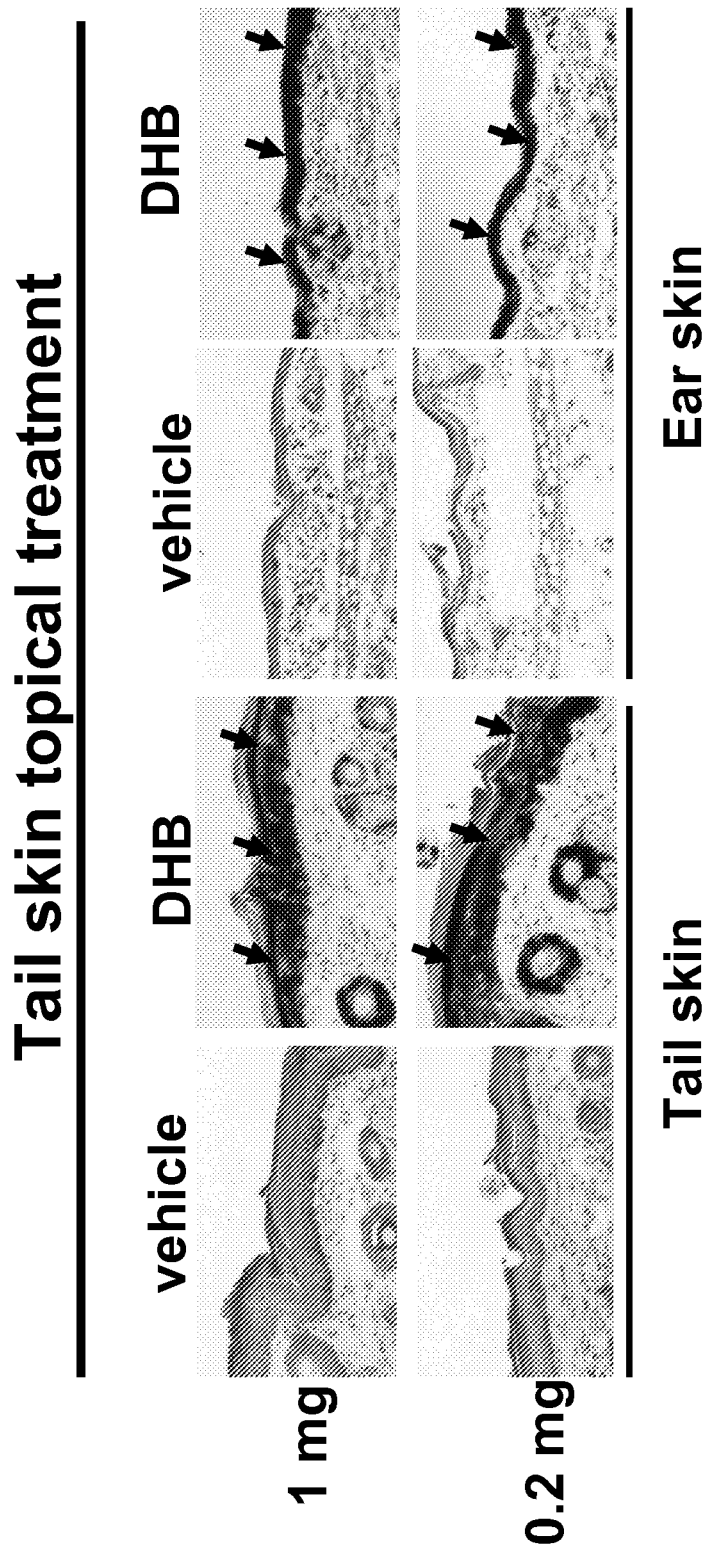

FIG. 7. Induction of Cre-ERM$^{Db}$ recombinase activity in skin keratinocytes of K14-Cre-ERM$^{Db}$/RosaR26R mice by topical DHB application to tail skin. Eight week-old K14-Cre-ERM$^{Db}$/RosaR26R mice were daily topically treated on tail skin with 1 or 0.2 mg DHB or vehicle from day 1 to day 5, and tail and ear sections taken at day 12 were X-Gal stained. Arrows point to some of the X-Gal stained keratinocytes.

Figure 8:
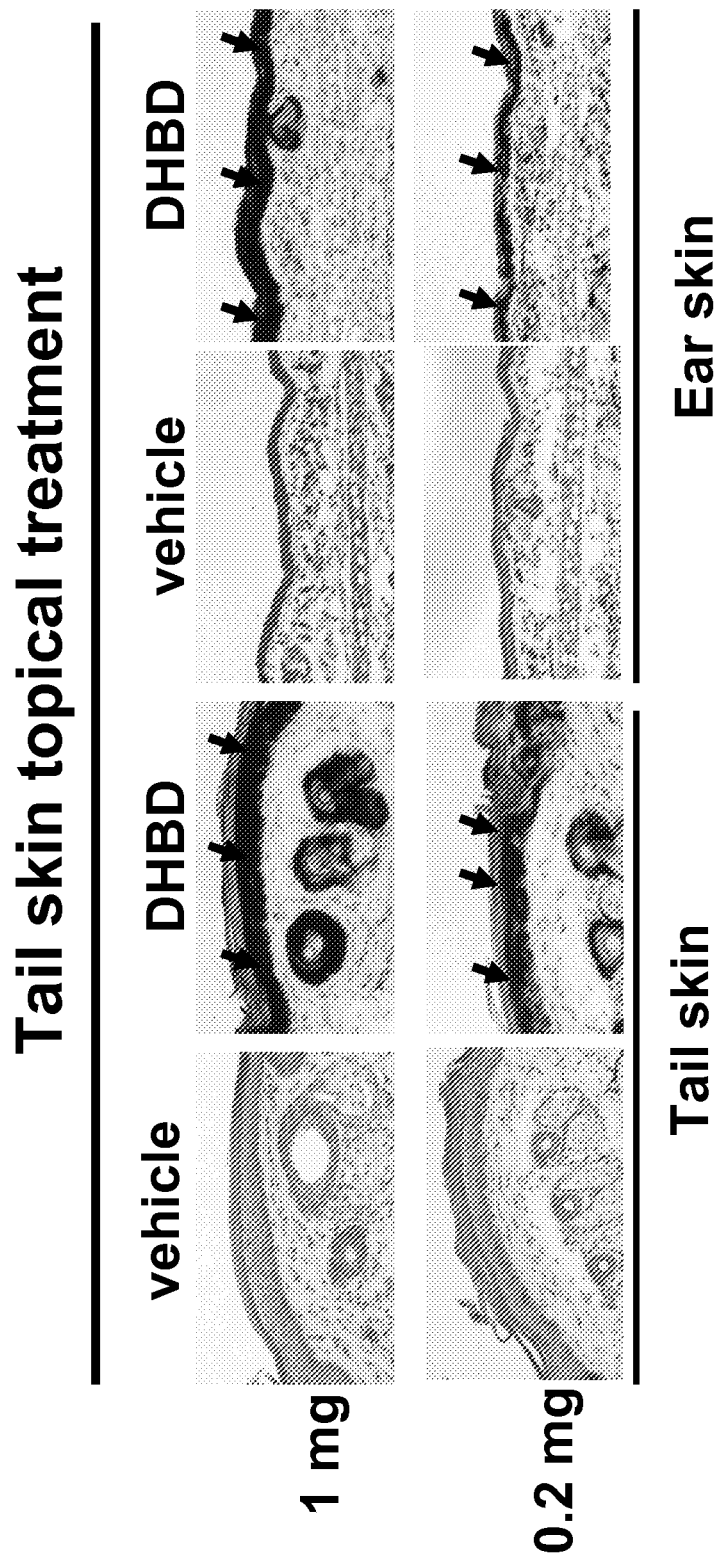

FIG. 8. Induction of Cre-ERM$^{Db}$ recombinase activity in skin keratinocytes of K14-Cre-ERM$^{Db}$/RosaR26R mice by topical DHBD application to tail skin. Eight week-old K14-Cre-ERM$^{Db}$/RosaR26R mice were daily topically treated on tail skin with 1 or 0.2 mg DHBD or vehicle from day 1 to day 5, and tail and ear sections taken at day 12 were X-Gal stained. Arrows point to some of the X-Gal stained keratinocytes.

Other advantages and embodiments will be apparent from the following examples that are merely given here for illustrating the present invention. In no way these examples limit the subject-matter of the present invention.

EXAMPLES

I—Materials and Methods

I-1—Plasmids pCre-ERM$^{Da}$, pCre-ERM$^{Db}$ and pCre-ERM$^{Dc}$ plasmids encoding Cre-ER fusion proteins with the hERα L346I, A350M, M388Q, G521S, Y526D, and L346I, A350M, M388Q, G400V, G521S, Y526D, and L346I, A350M, M388Q, G442Y, Y459N, L466S, G521S, Y526D mutations, respectively, were generated by PCR-based site-directed mutagenesis of pCre-ER (Metzger et al., 1995). pK14-Cre-ERM$^{Db}$ was generated by exchanging the 2 kb EcoRI DNA segment encompassing Cre-ER$^{T2}$ coding sequence from pK14-Cre-ER$^{T2}$ (Li et al., 2000), by a 2 kb EcoRI DNA segment isolated from pCre-ERM$^{Db}$.

I-2—Ligands 4,4' dihydroxylbenzyl (DHB) (Chockalingam et al., 2005), 4,4'-dihydroxylbenzyl dipivalate (DHBD), 4-hydroxy-4'-methoxybenzyl (HMB) and 4,4'-methoxybenzyl (MB) were dissolved in ethanol at 100 mg/ml. All-trans retinoic acid (RA), estradiol (E2) and 4-hydroxytamoxifen (OHT) were dissolved in ethanol, as described (Feil et al., 1997).

I-3—Establishment of Stable F9$^{+/(LNL)}$ Transfectants and Analysis of Cre-Mediated LoxP-Flanked DNA Excision F9$^{+/(LNL)}$ cells (Clifford et al., 1996; Metzger et al., 1995) were coelectroporated with 5 μg pCre-ER expression vectors and 1 μg pPGK-hyg, that had been digested with AseI and PvuII, respectively. Hygromycin-resistant clones were obtained as described (Metzger et al., 1995). To analyse Cre-mediated DNA excision, such clones were plated in 24-well plates at a density of 6×10$^3$ cells, and grown in the presence of 100 nM all-trans retinoic acid (RA). After 24 hrs, cells were exposed to vehicle (ethanol), DHB (60 nM-15 μM), estradiol (E2, 0.1 μM) or 4-hydroxytamoxifen (OHT, 0.1 μM) for 30 hrs. PCR amplification of a segment of the RXRα WT allele (+) and recombined RXRα (Δ) allele from their genomic DNA was carried out using the primers 5'-AAAACCTG-GATACAGAGCCCT-3' (SEQ ID No. 1) and 5'-TCAAAGC-CTACCTTCCCGCTTC-3' (SEQ ID No. 2) (+, ~300 bp; Δ, ~350 bp), as described (Feil et al., 1997).

I-4—Mice 5.4-kb NotI DNA segments of pK14-Cre-ERM$^{Db}$ were injected into FVBN zygotes to generate transgenic mice, as previously described (Li et al., 2000). K14-Cre-ERM$^{Db}$ and RosaR26R (Soriano, 1999) were genotyped as described (Metzger et al., 2005). For topical application, DHB, DHBD, HMB or MB dissolved in ethanol at 100 mg/ml was diluted two times in acetone, and 20 μl (1 mg) was daily applied on one cm$^2$ ear or tail skin for 5 days. For intraperitoneal and gavage administration, compounds dissolved in ethanol were diluted at 10 mg/ml in sunflower oil, and 100 μl were i.p. injected or orally administered to mice. Breeding and maintenance of mice were performed under institutional guidelines.

I-5—Immunocytochemistry

Cos-1 cells grown on Lab-TekII chamber slides (Nalge Nunc International) were transfected with 0.25 μg pCre-ERM expression vectors with Fugene, according to the manufacturer's instruction and treated with vehicle (ethanol) or 3 μM DHB for 24 hrs. After PFA fixation, cells transfected with pCre-ERM expression vectors were incubated over night at 4° C. with an anti-ER F3 monoclonal antibody (Ali et al., 1993) (1:1000 dilution), and revealed with CY3-conjugated goat anti mouse antibodies (1:200 dilution).

I-6—Immunohistochemistry and Histochemistry

Skin biopsies were embedded in OCT medium, immediately frozen on dry ice. Cre immunohistochemistry was performed on 10 μm-thick sections mounted on Superfrost slides. After a 5 min fixation in 4% PFA, sections were incubated in PBST (0.1% Tween 20 in PBS) containing 5% normal goat serum for 1 hr at room temperature. A 1/3000 dilution of rabbit polyclonal anti-Cre antibody (Kellendonk et al., 1999) was applied to the slide overnight at 4° C. After 4 washes in PBST (10 min each), sections were incubated for 2 hrs at 21° C. with a donkey anti-rabbit antibody coupled to the CY3 fluorochrome (Jackson Immunoresearch) at a 1/400 dilution. Slides were washed 4×3 min in PBST, and medium for fluorescence (Vectashield, Vector Laboratories) containing 0.01% DAPI (4',6-diamino-2-phenylindole dihydrochloride) was applied.

β-Galactosidase histochemistry was performed on 10 μm-thick frozen section, stained with X-Gal (5-bromo-4-chloro-3-indolyl β-D-galactoside), as described (Brocard et al., 1997).

II—Results

To determine whether the 4,4' dihydroxylbenzyl (DHB)-selective 4-S mutant ligand binding domain (LBD) of the human oestrogen receptor α (hERα) (Chockalingam et al., 2005) could regulate the Cre recombinase activity in mammalian cells, an expression vector pCre-ERM$^{Da}$, encoding Cre-ERM$^{Da}$, a fusion protein between Cre and the L346I, A350M, M388Q, G521S, Y526D mutant ERα LBD (FIG. 1), was generated. Immunocytochemistry of pCre-ERM$^{Da}$-transfected Cos-1 cells revealed that DHB induced Cre-ERM$^{Da}$ protein nuclear translocation (data not shown).

The recombinase activity of the chimeric protein was tested in genetically modified RXRα$^{+/(LNL)}$ F9 cells, bearing a LoxP-flanked (floxed) neomycin gene insertion in one RXRα allele (Clifford et al., 1996). To this end, RXRα$^{+/(LNL)}$ F9 cells were electroporated with pCre-ERM$^{Da}$ and a vector expressing a hygromycin-resistance gene. 29 pCre-ERM$^{Da}$-hygromycin-resistant clones were amplified and grown for 3 days in the absence or presence of 3 μM DHB. PCR analysis of genomic DNA from such recombinant F9 cells revealed Cre-mediated recombination in 20 pCre-ERM$^{Da}$-transfected clones, but it was DHB-dependent in only one of them (called hereafter Cre-ERM$^{Da}$/RXRα$^{+/(LNL)}$) (FIG. 2 and data not shown). However, even though DHB induced Cre-ERM$^{Da}$ recombinase activity, in the absence of ligand treatment higher background activity was detected in these cells than in Cre-ER$^{T2}$/RXRα$^{+/(LNL)}$ cells (FIG. 2 and data not shown).

In an attempt to reduce background recombinase activity, new chimeric proteins were generated between Cre and ERα ligand-binding domains containing additional mutations (e.g. Cre-ERM$^{Db}$ and Cre-ERM$^{Dc}$, see FIG. 1).

Immunocytochemistry of Cos-1 cells transfected with pCre-ERM$^{Db}$ revealed that Cre-ERM$^{Db}$ protein was located in the cytoplasm in the absence of ligand treatment, and that DHB induced its nuclear translocation (FIG. 3A). To characterise Cre-ERM$^{Db}$ recombinase activity, RXRα$^{+/(LNL)}$ F9 cells were electroporated with pCre-ERM$^{Db}$, and 41 pCre- ERM$^{Db}$-hygromycin-resistant clones were amplified and grown for 3 days in the absence or presence of 3 μM DHB. PCR analysis of genomic DNA from such recombinant F9 cells revealed Cre-mediated recombination in 19 pCre-ERM$^{Db}$-transfected clones, called hereafter Cre-ERM$^{Db}$/RXRα$^{+/(LNL)}$. Interestingly, 2 of such clones did not exhibit any recombinase activity in the absence of DHB treatment (FIGS. 3B and 4, and data not shown).

Immunocytochemistry revealed that DHB also induced translocation of Cre-ERM$^{Dc}$ from the cytoplasm to the nucleus (data not shown). Morover, electroporation of RXRα$^{+/(LNL)}$ F9 cells with the Cre-ERM$^{Dc}$ expression vector generated 54 hygromycin-resistant clones, amongst which 9 exhibited Cre-mediated recombinase activity, and in one of them, it was strictly DHB-dependent (FIG. 4, and data not shown).

The recombinase activity of Cre-ERM$^{Db}$ was further analysed in one of the two Cre-ERM$^{Db}$/RXRα$^{+/(LNL)}$ clones in the absence of ligand, as well as in the presence of DHB (3 μM), oestradiol (E2, 0,1 μM) and 4-hydroxytamoxifen (OHT, 0.1 μM). In agreement with screening data, no recombinase activity was seen in the absence of ligand, and DHB efficiently induced Cre-mediated floxed DNA excision (FIG. 3B). In contrast, neither E2 nor OHT induced any recombinase activity, and E2 did not alter DHB-induced Cre-mediated recombination (FIG. 3B).

To investigate whether DHB efficiently induced the recombinase activity of Cre-ERM$^{Db}$ in vivo, K14-Cre-ERM$^{Db}$ transgenic mice, expressing Cre-ERM$^{Db}$ under the control of the cytokeratin K14 promoter that is selectively active in basal keratinocytes of epidermis and of other stratified epithelia (Vassar et al., 1989), were generated (FIG. 5A). Out 10 founder mice, 9 transmitted the transgene through the germ line, and 4 expressed Cre-ERM$^{Db}$ in epidermal keratinocytes (FIG. 5B, data not shown).

The efficiency of DNA excision was analysed in one K14-Cre-ERM$^{Db}$ trangenic mouse line, using RosaR26R reporter mice, that express β-galactosidase after Cre-mediated DNA recombination (Soriano, 1999). DHB (1 mg) was topically applied to one ear of eight week-old bigenic K14-Cre-ERM$^{Db}$/RosaR26R mice from D1 to D5. X-Gal staining of sections of the DHB-treated ear sampled at D12 revealed that most, if not all epidermal keratinocytes from the treated ear expressed β-galactosidase, whereas no β-galactosidase activity was revealed on an ear biopsy taken before DHB or after vehicle application (FIG. 5C, and data not shown).

Moreover, gavage (2 mg/day for 5 days) or intraperitoneal (ip) injection (1 mg/day for 5 days) of K14-Cre-ERM$^{Db}$/RosaR26R mice with DHB also induced (β-galactosidase expression in epidermal keratinocytes (FIG. 5D and data not shown). Interestingly, two hours after 1 mg DHB i. p. administration, plasma levels reached 0.55 μg/ml, but were undetectable 22 hours later, indicating a high in vivo clearance of DHB.

Vehicle- and DHB-i. p. treated mice from D1-D5 had similar body weight at D5 and D19 (data not shown). Moreover, blood hematology and plasma biochemical profiles at D19 did not reveal major difference (see Table 1 below), and no histological defects were observed in liver of DHB-treated mice (data not shown), thus indicating that DHB does not interfere with mouse physiology.

TABLE 1

Blood hematology and plasma biochemical profile (means +/− SD) at D19 in mice daily ip injected with vehicle and 1 mg DHB from D1 to D5 (n = 3 mice for each gender).

| | male | | | | female | | |
|---|---|---|---|---|---|---|---|
| vehicle | vehicle | DHB | p | | vehicle | DHB | p |
| Glucose (mmol/l) | 27.2 +/− 3.9 | 21.4 +/− 7.2 | 0.31 | | 19.5 +/− 5.2 | 18.7 +/− 3.5 | 0.84 |
| Total protein (g/l) | 44.0 +/− 1.7 | 48.3 +/− 7.1 | 0.40 | | 45.5 +/− 0.7 | 48 +/− 2.6 | 0.24 |
| Albumin (g/l) | 25.7 +/− 0.6 | 27.3 +/− 3.5 | 0.5 | | 27.0 +/− 1.0 | 28.7 +/− 0.6 | 0.08 |
| HDL (U/l) | 546.0 +/− 172.7 | 1238 +/− 415 | 0.09 | | 1035.3 +/− 249.4 | 1081.0 +/− 699.6 | 0.91 |
| Cholesterol (mmol/l) | 2.1 +/− 0.2 | 2.2 +/− 0.2 | 0.84 | | 1.7 +/− 0.1 | 1.8 +/− 0.1 | 0.21 |
| Triglycerides (mmol/l) | 0.6 +/− 0.2 | 0.8 +/− 0.2 | 0.24 | | 0.6 +/− 0.1 | 0.6 +/− 0.1 | 1 |
| ASAT (U/l) | 107.7 +/− 33.5 | 194 +/− 45.5 | 0.06 | | 131.0 +/− 49.7 | 143.3 +/− 91.3 | 0.85 |
| ALAT (U/l) | 18.0 +/− 2.6 | 34.7 +/− 17.5 | 0.24 | | 19.7 +/− 3.2 | 27.7 +/− 2.9 | 0.47 |
| ALP (U/l) | 97.7 +/− 6.0 | 114.3 +/− 8.1 | 0.05 | | 117.7 +/− 10.1 | 137.0 +/− 14.1 | 0.13 |
| Bilirubin (mmol/l) | 1.6 +/− 0.6 | 2.0 +/− 0.3 | 0.42 | | 1.4 +/− 0.8 | 1.3 +/− 0.4 | 0.79 |
| Uric acid (mmol/l) | 106.3 +/− 12.1 | 235.7 +/− 132.5 | 0.23 | | 204.7 +/− 101.8 | 193.0 +/− 58.4 | 0.87 |
| Na (mmol/l) | 147.0 +/− 1.7 | 149.7 +/− 6.1 | 0.51 | | 148 +/− 6.9 | 152 +/− 1.0 | 0.42 |
| K (mmol/l) | 6.1 +/− 1.4 | 5.9 | | | 4.7 +/− 0.5 | 5.8 +/− 0.5 | 0.06 |
| Cl (mmol/l) | 111.7 +/− 1.2 | 113.3 +/− 3.1 | 0.45 | | 113.3 +/− 3.1 | 114.7 +/− 0.6 | 0.53 |
| Phosphorus (mmol/l) | 3.4 +/− 0.6 | 3.6 +/− 0.6 | 0.76 | | 2.8 +/− 0.8 | 3.2 +/− 0.1 | 0.47 |
| Magnesium (mmol/l) | 1.0 +/− 0.1 | 1.2 +/− 0.2 | 0.40 | | 1.8 +/− 0.9 | 1.5 +/− 0.1 | 0.72 |
| Iron (mmol/l) | 19.2 +/− 2.7 | 24.9 +/− 1.4 | 0.05 | | 19.7 +/− 4.1 | 25.6 +/− 3.9 | 0.14 |
| WBC (10$^3$/ml) | 4.6 +/− 1.2 | 8.7 +/− 4.6 | 0.27 | | 4.4 +/− 1.1 | 3.5 +/− 1.6 | 0.47 |
| RBC (10$^6$/ml) | 8.2 +/− 0.4 | 8.7 +/− 0.8 | 0.33 | | 8.2 +/− 0.2 | 8.2 +/− 0.3 | 0.93 |
| HGB (g/dl) | 13.1 +/− 0.8 | 14.0 +/− 1.3 | 0.41 | | 13.6 +/− 0.4 | 13.3 +/− 0.8 | 0.63 |
| HCT (%) | 37.7 +/− 2.5 | 40.0 +/− 3.7 | 0.43 | | 39.7 +/− 0.7 | 38.9 +/− 2.3 | 0.59 |
| MCV (fl) | 46.2 +/− 1.2 | 45.8 +/− 0.5 | 0.67 | | 48.4 +/− 0.7 | 47.2 +/− 0.9 | 0.13 |
| MCH (pg) | 16.1 +/− 0.5 | 16.0 +/− 0.2 | 0.84 | | 16.5 +/− 0.1 | 16.1 +/− 0.2 | 0.08 |
| MCHC (g/dl) | 34.9 +/− 0.5 | 34.9 +/− 0.1 | 0.84 | | 34.1 +/− 0.4 | 34.2 +/− 0.2 | 0.73 |

WBC, white blood cell counts;
RBC, red blood cell counts;
HGB, hemoglobin;
HCT, hematocrit;
erythrocyte indexes:
MCV, mean corpuscular volume;
MCH, mean corpuscular hemoglobin;
MCHC, mean corpuscular hemoglobin concentration.

Ear treatment at 1 mg/day for 5 days of the non-oestrogenic compound DHB or MB to transgenic K14-Cre-ERM$^{Db}$/RosaR26R mice also efficiently induced Cre-mediated recombination in keratinocytes expressing Cre-ERM$^{Db}$ recombinase (FIG. 6).

Moreover, daily tail topical treatment of K14-Cre-ERM$^{Db}$/RosaR26R mice at 1 or 0.2 mg DHB or DHBD for 5 days induced efficient Cre-mediated recombination in Cre-ERM$^{Db}$-expressing keratinocytes of tail treated skin, as well as in those of ear skin (FIGS. 7 and 8), thus demonstrating that low doses of DHB and DHBD efficiently induce recombination not only in cells from the treated regions, but also in distal Cre-ERM$^{Db}$-expressing cells.

REFERENCES

Ali, S., Lutz, Y., Bellocq, J. P., Chenard-Neu, M. P., Rouyer, N., and Metzger, D. (1993). Production and characterization of monoclonal antibodies recognising defined regions of the human oestrogen receptor. Hybridoma 12, 391-405.

Brocard, J., Warot, X., Wendling, O., Messaddeq, N., Vonesch, J. L., Chambon, P., and Metzger, D. (1997). Spatio-temporally controlled site-specific somatic mutagenesis in the mouse. Proc Natl Acad Sci USA 94, 14559-14563.

Chockalingam, K., Chen, Z., Katzenellenbogen, J. A., and Zhao, H. (2005). Directed evolution of specific receptor-ligand pairs for use in the creation of gene switches. Proc Natl Acad Sci USA 102, 5691-5696.

Clifford, J., Chiba, H., Sobieszczuk, D., Metzger, D., and Chambon, P. (1996). RXRalpha-null F9 embryonal carcinoma cells are resistant to the differentiation, anti-proliferative and apoptotic effects of retinoids. Embo J 15, 4142-4155.

Feil, R. (2007). Conditional somatic mutagenesis in the mouse using site-specific recombinases. Handb Exp Pharmacol, 3-28.

Feil, R., Wagner, J., Metzger, D., and Chambon, P. (1997). Regulation of Cre recombinase activity by mutated estrogen receptor ligand-binding domains. Biochem Biophys Res Commun 237, 752-757.

Fink, B. E., Mortensen, D. S., Stauffer, S. R., Aron, Z. D., and Katzenellenbogen, J. A. (1999). Novel structural templates for estrogen-receptor ligands and prospects for combinatorial synthesis of estrogens. Chem Biol 6, 205-219.

Kellendonk, C., Tronche, F., Casanova, E., Anlag, K., Opherk, C., and Schutz, G. (1999). Inducible site-specific recombination in the brain. J Mol Biol 285, 175-182.

Li, M., Indra, A. K., Warot, X., Brocard, J., Messaddeq, N., Kato, S., Metzger, D., and Chambon, P. (2000). Skin abnormalities generated by temporally controlled RXRalpha mutations in mouse epidermis. Nature 407, 633-636.

Metzger, D., and Chambon, P. (2001). Site- and time-specific gene targeting in the mouse. Methods 24, 71-80.

Metzger, D., Clifford, J., Chiba, H., and Chambon, P. (1995). Conditional site-specific recombination in mammalian cells using a ligand-dependent chimeric Cre recombinase. Proc Natl Acad Sci USA 92, 6991-6995.

Soriano, P. (1999). Generalized lacZ expression with the ROSA26 Cre reporter strain. Nat Genet. 21, 70-71.

Vassar, R., Rosenberg, M., Ross, S., Tyner, A., and Fuchs, E. (1989). Tissue-specific and differentiation-specific expression of a human K14 keratin gene in transgenic mice. Proc Natl Acad Sci USA 86, 1563-1567.

Zambrowicz, B. P., and Sands, A. T. (2003). Knockouts model the 100 best-selling drugs—will they model the next 100? Nat Rev Drug Discov 2, 38-51.

Picard D. (1994) Regulation of protein function through expression of chimaeric proteins. Curr Opin Biotechnol. 5:511-5.

Fussenegger (2001) The impact of mammalian gene regulation concepts on functional genomic research, metabolic engineering, and advanced gene therapies. Biotechnol. Prog. 17 : 1-51.

Mattioni T, Louvion J F, Picard D. (1994) Regulation of protein activities by fusion to steroid binding domains. Methods Cell Biol. 43 A:335-52.

Harvey D M and Caskey C T. (1998) Inducible control of gene expression: prospects for gene therapy. Curr Opin Chem. Biol. 2(4):512-8.

D. Metzger, M. Li and P. Chambon. (2005) Targeted somatic mutagenesis in the mouse epidermis. Epidermal Cells: Methods Mol. Biol. The humana Press Inc. Ottawa, N.J., USA, 289.329-340.

The invention claimed is:

1. A method for controlling the biological activity of a protein of interest in a vertebrate cell, said protein of interest in a vertebrate cell being expressed in said cell in the form of a fusion protein wherein said fusion protein comprises:

(i) a polypeptide comprising a mutated form of the ligand binding domain of the human oestrogen receptor alpha of sequence SEQ ID NO: 3, wherein said mutated form has the mutations L346I, A350M, M388Q, G442Y, Y459N, L466S, G521S and Y526D relative to SEQ ID NO: 3, wherein said polypeptide selectively binds a synthetic ligand devoid of oestrogenic and anti-oestrogenic activities, and (ii) said protein of interest, wherein the biological activity of said protein of interest is induced by said synthetic ligand, said method comprising:

a) providing a vertebrate cell expressing said fusion protein;

b) contacting said vertebrate cell with said synthetic ligand to induce the biological activity of said fusion protein in said cell; and c) recovering the biological activity of said fusion protein in said vertebrate cell, wherein said protein of interest is selected from the group consisting of cytokines, hormones. transcription factors, signaling modules, enzymes oncoproteins and tumor-suppressor proteins.

2. The method according to claim 1, wherein said fusion protein is encoded by a fusion gene under the control of expression elements ensuring a spatially controlled expression thereof in said vertebrate cell.

3. The method according to claim 2, wherein said fusion gene is integrated into at least one chromosome of said vertebrate cell.

4. The method according to claim 2, wherein said fusion gene is integrated into at least one extrachromosomal expression vector in said vertebrate cell.

5. The method according to claim 1, wherein said protein of interest is a site specific recombinase protein.

6. The method according to claim 5, wherein said site-specific recombinase protein is selected from the group consisting of the Cre recombinase of bacteriophage P1, the FLP recombinase of *Saccharomyces cerevisiae*, the R recombinase of *Zygosaccharomyces rouxii* pSR1, the A recombinase of *Kluyveromyces drosophilarium* pKD1, the A recombinase of *Kluyveromyces waltii* pKW1, the integrase λInt, the recombinase of the GIN Recombination system of the Mu phage, the bacterial β recornbinase, and variants thereof.

7. The method according to claim 6, wherein said vertebrate cell further comprises one or more recognition sites for said site-specific recombinase protein.

8. The method according to claim 7, wherein said site-specific recombinase protein is the Cre recombinase of bacteriophage P1 and said recognition sites are selected from the group consisting of the sequences Lox P, Lox 66, Lox 71, Lox 511, Lox 512, and Lox 514.

9. The method according to claim 7, wherein said site-specific recombinase protein is the FLP recombinase of *Saccharomyces cerevisiae* and said recognition sites are the FRT sequences.

10. The method according to claim 7, wherein said recognition sites are inserted into one or more gene or intergenic DNA sequences of interest.

11. The method according to claim 10, wherein said method is used for carrying out spatio-temporally-controlled site-specific recombinations of said DNA sequences of interest in a vertebrate, wherein, in said step c), recombination of said DNA sequences of interest is obtained in said vertebrate cell.

12. The method according to claim 11, wherein said recombination is selected from the group consisting of: excisions, insertions, inversions, deletions, and translocations.

13. The method according claim 1, wherein said synthetic ligand is chosen from the group consisting of 4,4'-dihydroxybenzyl (DHB), 4,4'-dihydroxylbenzyl dipivalate (DHBD), 4-hydroxy-4'-methoxybenzyl (HMB), 4,4'-methoxybenzyl (MB), and 2,4-di(4-hydroxyphenyl)-5-ethylthiazole (L9).

14. The method according to claim 1, wherein said vertebrate cell is from a vertebrate selected from the group consisting of: birds, fishes, and mammals including humans, bovines, porcines, caprines, ovines, equines, rodents such as mice and rats.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: artificial
<220> FEATURE:
<223> OTHER INFORMATION: PCR primers

<400> SEQUENCE: 1
aaaacctgga tacagagccc t                                     21

<210> SEQ ID NO 2
<211> LENGTH: 22
<212> TYPE: DNA
<213> ORGANISM: artificial
<220> FEATURE:
<223> OTHER INFORMATION: PCR primers

<400> SEQUENCE: 2
tcaaagccta ccttcccgct tc                                    22
```

-continued

<210> SEQ ID NO 3
<211> LENGTH: 595
<212> TYPE: PRT
<213> ORGANISM: Homo sapiens
<220> FEATURE:
<221> NAME/KEY: misc_feature
<223> OTHER INFORMATION: Wild-type Human estrogen receptor a protein
      sequence

<400> SEQUENCE: 3

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
```

-continued

```
                355                 360                 365
Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595
```